United States Patent [19]

Weldon et al.

[11] Patent Number: 5,529,278
[45] Date of Patent: Jun. 25, 1996

[54] FLUID ACCESS AND FLOW CONTROL VALVE

[75] Inventors: Thomas D. Weldon, Gainsville; Charles E. Larsen, Cumming; Jonathan J. Rosen, Alparette, all of Ga.

[73] Assignee: Novoste Corporation, Norcross, Ga.

[21] Appl. No.: 154,944

[22] Filed: Nov. 19, 1993

[51] Int. Cl.$^6$ .................................................. F16K 7/02
[52] U.S. Cl. ..................................... 251/4; 251/349
[58] Field of Search ............................. 251/4, 7, 349, 251/353; 138/45

[56] References Cited

U.S. PATENT DOCUMENTS

| | | |
|---|---|---|
| 2,442,746 | 6/1948 | Anderson et al. |
| 3,072,151 | 1/1963 | Quercia .................................. 251/4 X |
| 3,095,175 | 6/1963 | Iketani ...................................... 251/4 |
| 3,685,786 | 8/1972 | Woodson .................................. 251/4 |
| 4,351,510 | 9/1982 | Welker . |
| 5,215,538 | 6/1993 | Larkin . |
| 5,226,898 | 7/1993 | Gross . |
| 5,242,432 | 9/1993 | DeFrank et al. |
| 5,338,313 | 8/1994 | Mollenauer et al. ................ 251/4 X |

FOREIGN PATENT DOCUMENTS

| | | | |
|---|---|---|---|
| 0510851A1 | 4/1991 | European Pat. Off. ....... A61M 39/06 |
| 355675 | 6/1922 | Germany ................................... 251/4 |

OTHER PUBLICATIONS

European Search Report, Application No. EP 94 11 8148
Annex to the European Search Report on European Patent Application No., Application No. EP 94 11 8148.

*Primary Examiner*—John C. Fox
*Attorney, Agent, or Firm*—Cook, McFarron & Manzo Ltd.

[57] ABSTRACT

A flow control valve is described comprised of first and second rigid members and a resilient single or multi stage valve element disposed between the rigid members. A fluid flow path is defined through the rigid members and through or around the valve element to provide a continuous flow path through the valve. The rigid members are movable relative to each other between a first position and a second position. The valve element is sufficiently compressed by the rigid members when they are in the first position so as to close the flow path through or around the valve element. The valve element is sufficiently relaxed when the rigid members are in the second position to allow fluid flow through the flow path through or around the valve element.

18 Claims, 6 Drawing Sheets

FLUID ACCESS AND FLOW CONTROL VALVE

The present invention relates to fluid flow control devices for regulating the flow of liquid or gas. More particularly, the present invention relates to flow control valves and valve elements for use therein that may be used to regulate the flow of liquid or gas therethrough by compression or deformation of the valve element.

BACKGROUND OF THE INVENTION

Flow control valves for liquid and gas come in many shape and sizes, and are made of a wide variety of materials depending on their intended use.

Typically, flow control valves such as butterfly valves and gate valves are used to control flow of fluid by moving a mechanical member into and out of the flow path to partially or completely block the flow path. Other types of valves, for example roller clamps used in medical intravenous apparatus, control flow by pinching the plastic tubing through which the fluid flows. Still other types of valves operate by controlling the length of the flow path, and therefore the resistance to flow, through the valve.

Despite the wide variety of valves that have been known or used heretofore, there is a continuing need for improved flow control valves that have cost, ease of use, functional, and other advantages compared to prior flow control valves.

SUMMARY OF THE INVENTION

The present invention is directed to such a new and improved flow control valve and valve element for use therein. In accordance with one embodiment of the present invention, the valve comprises a rigid housing including a fluid inlet, a fluid outlet, and a flow path between the inlet and outlet. The flow path includes a valve element chamber in which a resilient valve element is located. The housing is operable to change the size or shape of the valve element chamber between at least first and second chamber sizes. When the chamber is of the first size or shape, the valve element therein is sufficiently compressed that it blocks flow through the flow path. When the chamber is of the larger second size, the valve element is sufficiently relaxed to allow flow through the flow path.

The valve element in accordance with the present invention has at least a first valve body made of resilient material that defines, at least in part, a fluid inlet, a fluid outlet, and a flow path between the fluid inlet and outlet, whereby the size of the flow path may be varied by compression of the first valve body. In one embodiment of the valve element, the valve body has the inlet defined in one end of the body, the outlet defined in another end of the body, and the flow path extending through the valve body. In another embodiment, the flow path is defined at least part along the exterior surface of the valve body, which serves to define the flow path when in close contact of the interior surface of the valve element chamber within the valve housing. In either embodiment, the size of the flow path is controlled by the degree of compression of the valve body.

In accordance with yet a further embodiment of the present invention, the valve element includes a second valve body that is carried by the first valve body and is movable relative thereto. Preferably, the second valve body is carried by a plurality of spaced apart resilient legs that extend between the first and second valve bodies, and resiliently bias the second valve body in a position spaced from the first valve body. This dual valve body construction provides a two-stage valve element that allows on/off control by the second valve body and graduated flow control by the first valve body, or vice versa. For example, the two-stage valve element may be positioned within a valve element chamber in which the second valve body is resiliently biased to seat against the interior surface of the flow path, to normally block the flow of fluid therethrough. The second valve body may be unseated by pushing it away from the surface against which it is seated, for example, by engagement with the end of a male luer fitting that is inserted into the flow path through the inlet or outlet of the valve housing. When the second valve body is unseated, allowing flow through the valve housing, the flow is then controlled by the degree of compression of the first valve body. Alternatively, the first valve body may be used for on/off control, and the second valve body may be used as a graduated control for the flow of fluid through the valve housing.

The valve housing of the present invention preferably comprises a pair of rigid members that are relatively movable to vary the shape or size of the valve element chamber. Various embodiments of the rigid members are disclosed hereinafter for purposes of illustration, and not limitation. For example, one of the rigid members may comprise a tubular body, and the other rigid member may include a cylindrical projection that extends into the tubular body, with the valve element chamber defined therebetween. The size and shape of the valve element chamber may be varied by varying the distance that the projection extends into the tubular body. Similarly, various features are disclosed for holding the first and second rigid members in the desired axial position to maintain the compression of the valve element in the desired amount. For example, the rigid members may be threadedly connected to control the degree of extension of the projection into the tubular body, and thereby control the size and shape of the valve element chamber. Alternatively, arms may be provided on one of the rigid members, which contact retaining surfaces formed on the mating rigid member.

The foregoing summary is provided for the purpose of overview and introduction of the present invention. Not all features or aspects of the present invention are set forth in the summary, and reference must be made to attached drawings and detailed description set forth hereinafter for a complete description of these and the many other features of the present invention.

DESCRIPTION OF THE PREFERRED EMBODIMENT

Figure 1:
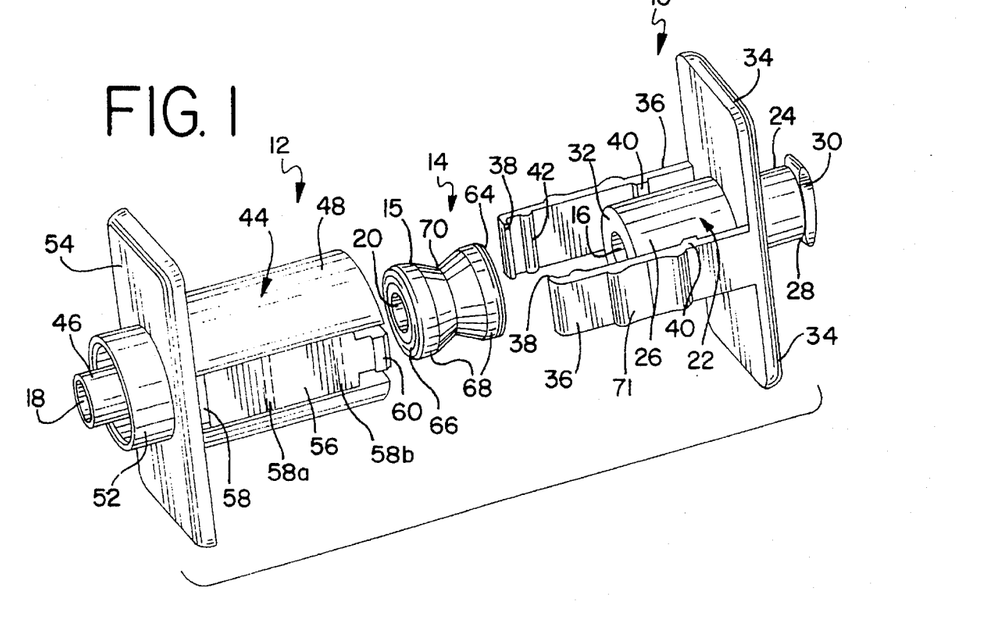
FIG. 1 is a perspective view showing the disassembled components of one embodiment of the flow control valve and valve element of the present invention.

As illustrated in FIG. 1, the flow control valve of the present invention comprises a first rigid member 10, a second rigid member 12 and a valve element 14 which is located between the first and second rigid members. The rigid members 10 and 12 and valve element 14 each have a center bore 16, 18 and 20, respectively, extending axially therethrough and together defining a flow path passageway through the flow control valve.

The first rigid member 10 has a generally cylindrical body portion 22 with a first end 24 and a second end 26. Bore 16 extends through the first rigid member 10 from end to end, generally coaxial with the cylindrical body portion 22.

Figure 2:
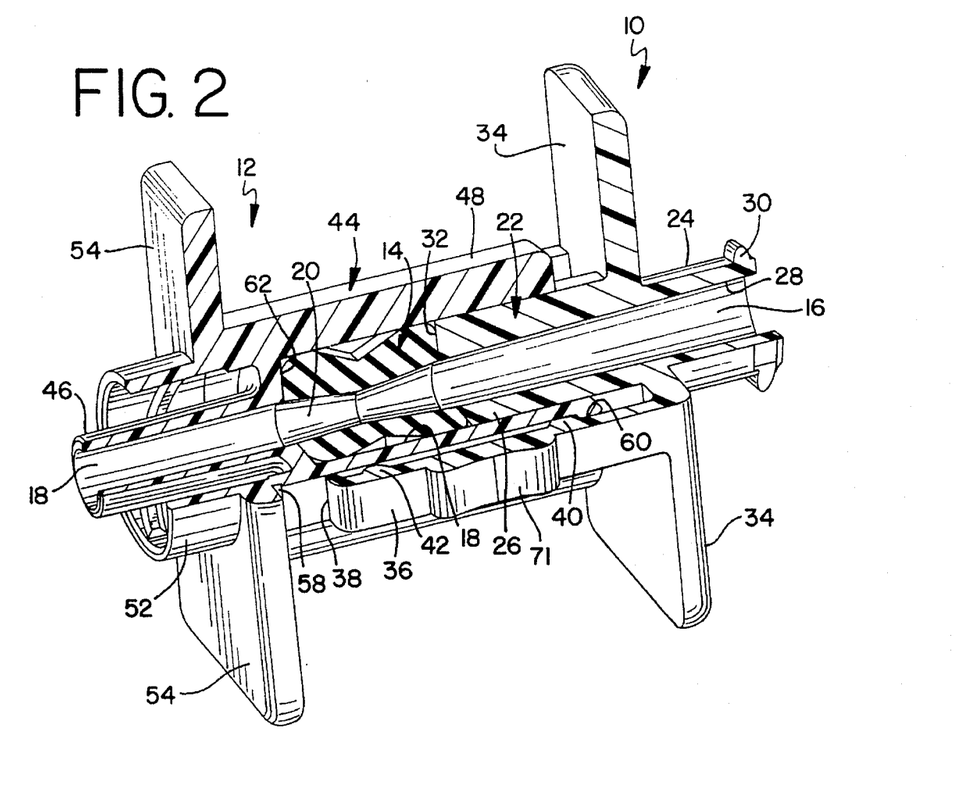
FIG. 2 is a perspective view, partially in cross-section, of the assembled flow control valve of FIG. 1, in an open flow position.

The first end 24 of the cylindrical body portion 22 is adapted for cooperating with any desired conduit and may embody a variety of forms without departing from the scope of the present invention. The means of attachment may be a pipe thread or a stub for attachment to plastic or rubber tubing or, as depicted in the attached drawings, it may take the form of a female luer 28 with a thread 30 facilitating a luer lock attachment. As best seen in FIG. 2, the interior of the bore 16 at the first end 24 is tapered to receive a correspondingly tapered male luer fitting. The second end 26 of the cylindrical body portion 22 terminates in a flat ring shaped surface 32 to contact and compress the valve element 14.

To facilitate operation of the flow control valve, one or more finger flanges 34 extend outwardly from the cylindrical body portion 22 of the first rigid member 10 intermediate first and second ends 24 and 26. The finger flanges 34, as depicted in FIG. 1, are rectangular in shape and are large enough to permit an individual to operate the flow control valve with the fingers of one hand.

To hold the first rigid member 10 and second rigid member 12 of the flow control valve together, at least one and preferably two retaining arms 36 extend from the finger flanges 34 generally parallel to and spaced from the cylindrical body portion 22. Each retaining arm 36 possesses a first inwardly directed rib or protrusion 38 at the free end of the retaining arm and a second inwardly directed rib or protrusion 40 located nearer to the base of the retaining arm 36. A third inwardly directed rib or protrusion 42 located between the first and second protrusions acts as a fulcrum for adjusting the valve position as will be more fully described hereinafter.

The second rigid member 12 of the flow control valve has a generally tubular body portion 44 with a first end 46 and a second end 48. Bore 18 extends through the second rigid member 12 from end to end, generally co-axial with said tubular body portion 44.

Again, to facilitate conduit attachment, the first end 46 of the second rigid member 12 is in the form of a tapered male luer which is insertable into a corresponding female luer fitting. A threaded locking ring 52 around the male luer fitting provides for threaded attachment to luer-lock counterpart on a female luer fitting. Alternative attachment mechanisms, as described above with respect to the first rigid member 10, are known in the art and may be used as means of attachment to the valve without departing from the scope of the present invention.

The second rigid member 12, like the first rigid member 10, possesses one or more finger flanges 54 that are located between the first end 46 and the second end 48 of the second rigid member 12. Like the finger flanges 34 of first rigid member 10, the finger flanges 54 of the second rigid member 12, are rectangular in shape and large enough to permit operation with the digits of one hand. Of course, alternative flange designs or shapes may be used without departing from the scope of the present invention.

Figure 3:
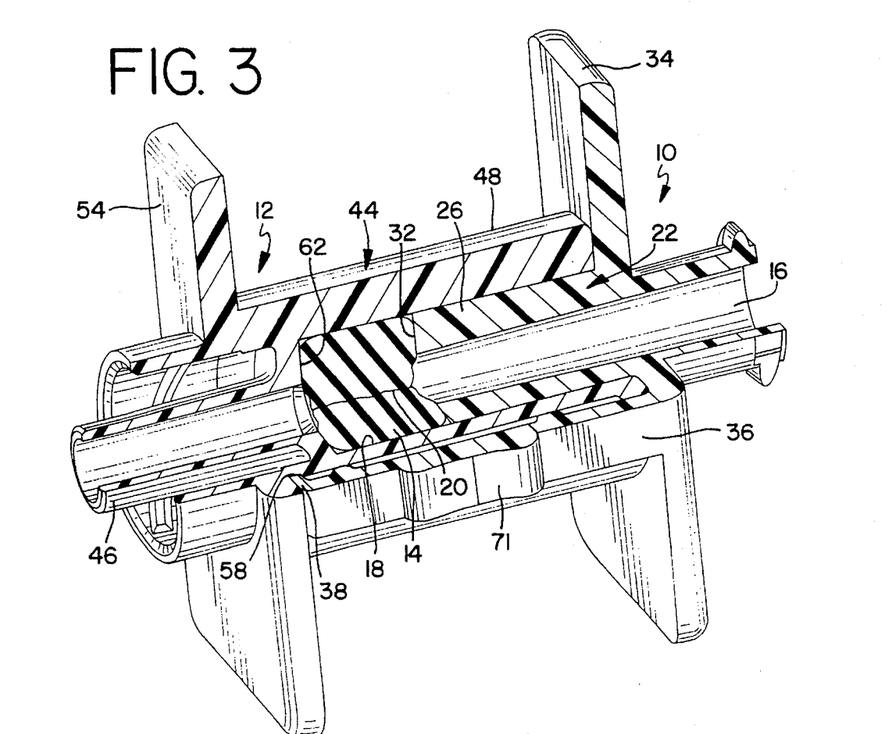
FIG. 3 is a perspective view, partially in cross-section, of the assembled flow control valve of FIG. 1, in a closed flow position.

To facilitate contact with the protrusions 38 and 40 of the retaining arms 36, flattened surfaces 56 are provided on opposite sides of the tubular body portion 44 and extend along the exterior of the tubular body portion between second end 48 and finger flanges 54. As best seen in FIG. 1, a notch 58 is provided in one end of the flattened surfaces 56 to receive rib 38 of the retaining arm and hold the rigid members in a closed valve position (as seen in FIG. 3). The other end of the flattened area has a raised rib 60 for abutment against the rib or protrusion 40 of the retaining arm to prevent complete separation of the rigid members 10 and 12 when the valve is in the open position (as seen in FIG. 2).

The interior bore 18 of the tubular body portion 44 is sized to receive both the valve element 14 and second end surface 32 of cylindrical body portion 22. In order to house the valve element 14 within bore 18 and to slidably and coaxially receive the second end 26 of the first rigid member 10, bore 18 has an internal diameter slightly larger than the external diameter of the second end 26 of the cylindrical body portion 22. When the cylindrical body portion 22 of the first rigid member 10 is located within the bore 18 of the second rigid member 12, an internal valve element chamber is defined between the end surface 32 of the cylindrical body portion 22, interior shoulder 62 in the second rigid member 12 and the inside surface of bore 18. The valve element 14 is located within this chamber.

Figure 8:
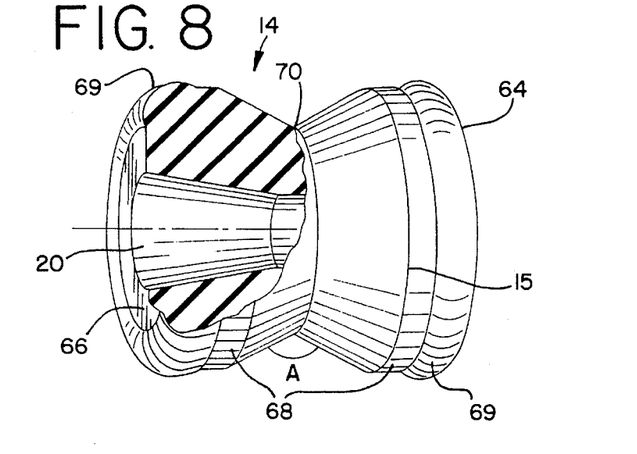
FIG. 8 is a perspective view, partially in cross-section, of the valve element which is shown in FIGS. 1, 2, 3 and 7.

Flow through the flow control valve is regulated by the varying the compression of valve element 14 to control the size of bore 20 therein. To permit compression and thus variation in the size of bore 20, the valve element 14 preferably has a first valve body 15 of generally hourglass configuration, as best seen in FIGS. 1 and 8. More specifically, first valve body 15 has flat ring-like first and second end surfaces 64 and 66, respectively, and generally cylindrical side surfaces 68 that merge into rounded corner 69 of slightly larger diameter located at each end. The diameter of the valve element may be sized such that the cylindrical side surfaces 68 and/or the rounded corners 69 sealingly engage against the inside surface of the valve chamber, for example, to form fluid seals with the surface of bore 18 of the tubular body portion 22.

Between the cylindrical surfaces 68, a V-shaped cleft 70 extends around the exterior surface of valve element 14. Cleft 70 allows compression of valve element 14 to occur about a preferential fold line located generally at the apex of the cleft. As best understood, because of the aforedescribed construction, compression of valve element 14 causes bore 18 to constrict in a uniform and iris-like manner. This allows flow through the valve element to be controlled without introducing undesirable turbulence to the flow. Accordingly, in situations where the flow through the valve is laminar, it is believed that flow can be controlled without greatly disrupting the laminar flow.

Rigid members 10 and 12 are preferably made of a rigid moldable plastic, such as nylon, polyethylene or the like, although any other suitable material may be used. Valve element 14 is preferably made of a resilient or elastomeric material, such as silicone or urethane.

Referring to FIG. 2, when the valve of FIG. 1 is assembled, the cylindrical body portion 22 of first rigid member 10 extends into bore 18 of the tubular body portion of second rigid member 12. The end surface 32 of the cylindrical body portion 22, interior shoulder 62 in the second rigid member 12 and the inside surface of bore 18 define the aforedescribed valve element chamber wherein valve element 14 is positioned. Shoulder 62 and second end surface 32 abut respectively the circular ends 66 and 64 of the valve element 14 with sufficient pressure that bores 18, 20 and 16 form a continuous, leak free, flow path through the assembled flow control valve.

In the fully open valve position shown in FIG. 2, the protrusions 40 of the retaining arms 36 abut the raised ribs 60 in the otherwise flat surfaces 56 of the second rigid member 12 and prevent the cylindrical and tubular body portions 22 and 44 from separating under any axial force exerted by the valve element.

FIG. 3 shows the flow control valve of FIGS. 1 and 2 in a fully closed position. In that position, the rigid members have been moved closer together along a common axis to reduce the size of the valve element chamber such that the valve element 14 is sufficiently compressed within bore 18 between shoulder 62 and the end surface 32 of the first rigid member 10, causing the complete closure of bore 20. Because the valve element 14 is made of a resilient material, when it is compressed it exerts axial expansion forces against the shoulder 62 and end surface 32. Separation of the rigid members 10 and 12 is prevented, however, by the protrusions 38 of the retaining arms 36 which are engaged in the notches 58 provided in the flat surfaces 56 of the second rigid member 12. Specifically, the distance between protrusions 38 of retaining arms 36 is slightly less than the distance between the flat surfaces 56 of tubular body portion 44, so that there is a inwardly directed spring-like force that tends to retain the protrusions 38 in the notches 58.

Alternatively, several additional notches, such as 58a and 58b depicted in dashed lines in FIG. 1, may be provided at spaced locations along the length of the flattened surface 56 between notch 58 and raised rib 60, corresponding to selected different sizes of the value element chamber and corresponding degrees of compression of the valve element 14 with different degrees of flow path restriction. These additional notches would receive protrusion 38 of the retaining arms 36 so as to hold the valve members at selected positions between the fully open (FIG. 2) and fully closed (FIG. 3) valve positions previously discussed, so that intermediate flow rates may be maintained through the flow control valve.

The simple three-piece componentry of the above-described flow control valve allows it to be assembled without requiring special tools or techniques. Indeed, the molded rigid members and valve element may be combined to form the assembled valve either by hand or by machine to meet the needs of the individual manufacturer.

To assemble the valve, valve element 14 is placed within bore 18 of the second end 48 of the tubular body portion 44 such that the flat surface 56 of the valve element 14 contacts shoulder 62 of the second rigid member 12. The valve element may be sized, as described earlier, so that it sealingly engages against the inside surface of bore 18, although this is not absolutely necessary if the ends of the valve element form fluid seals with the shoulder 62 and the end surface of the cylindrical body portion 22. The second end 26 of the cylindrical body portion 22 of first rigid member 10 is then inserted into bore 18 and aligned so that the retaining arms 36 of the first rigid member 10 contact the flat surfaces 56 of the tubular body portion 44 of the second rigid member 12. To complete assembly, the rigid members 10 and 12 are pressed together until the protrusions 40 of the retaining arms 36 slip over the raised ribs 60 of the second rigid members 12, preventing the rigid members from separating. The leading edge of protrusion 40 may be tapered to allow the protrusion to more easily slide over rib 60 during assembly.

Once the open flow control valve is assembled as shown in FIG. 2, it may be operated with the thumb and fingers of one hand by pressing the finger flanges 34 of the first rigid member 10 toward the finger flanges 54 of the second rigid member 12. When so pressed, the second end 26 of the cylindrical body portion 22 advances from an open first position to a position further inside the tubular body portion 44, compressing valve element 14 between the end surface 32 of the cylindrical body portion 22 and the shoulder 62 of the tubular body portion 44 and causing bore 20 to constrict, reducing the fluid flow through the valve. When the second end 26 of the cylindrical body portion 22 is inserted a distance within the tubular body portion 44 corresponding to closure of the bore 20 through valve element 14, protrusions 38 of the retaining arms 36 engage into the notches 58 of the tubular body portion 44, thus holding the rigid members 10 and 12 in their closed valve orientation, as best seen in FIG. 3.

Figure 4:
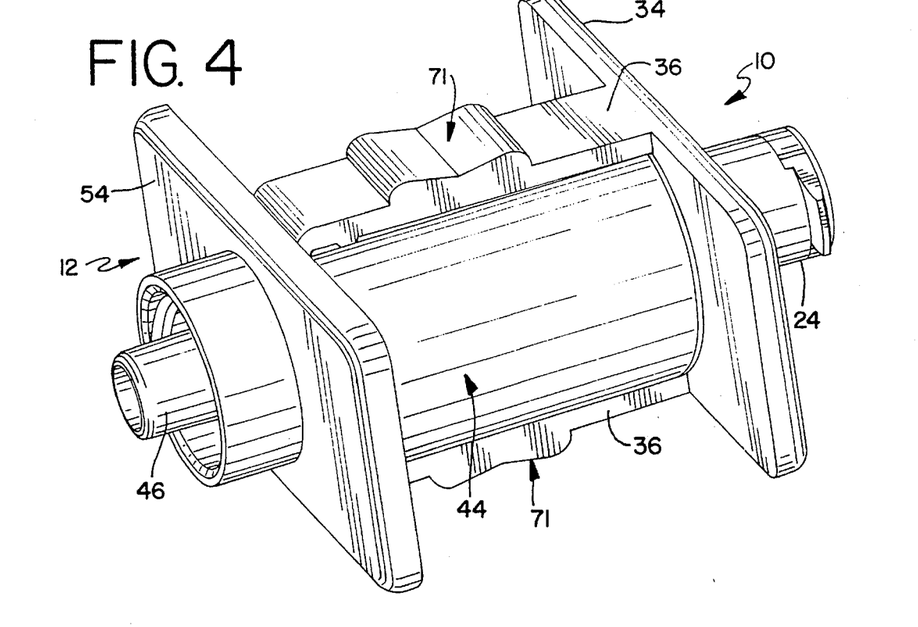
FIG. 4 is a perspective view of the flow control valve of FIG. 1 in the closed position.

To open the valve when it is in its closed position, inward pressure is applied to the external surface of retaining arms 36 intermediate fulcrum rib 42 and protrusion 40 of retaining arms 36, as shown in FIG. 4. This pressure will bend the retaining arm 36 between fulcrum rib 42 and protrusion 40, causing the engaged protrusion 38 to be lifted away from tubular body portion 44 and out of notch 58. Finger grip surfaces 71 may be provided at the desired location, between the fulcrum rib 42 and protrusion 40, on the exterior surface of the retaining arms to facilitate release of the valve from the closed position.

Once protrusion 38 is disengaged from notch 58, axial force from the compressed resilient valve element 14 will normally push the two rigid members 10 and 12 apart until the raised ribs 60 of the tubular body portion 44 contact protrusions 40 of the retaining arms 36, as is best shown in FIG. 2, thus allowing the bore 20 to return to its fully open state and once more permitting flow through the flow control valve. If additional intermediate positions 58a and 58b are provided, the rigid members may be expected to separate until the protrusion 38 engages into one of such intermediate notches.

The preferred valve element 14 is best seen in FIGS. 1 and 8. As better seen in FIG. 8, the valve element has a body of single piece molded construction. The cleft 70 extends at an angle A, and the valve element is believed to function best when the angle of the cleft is between about 60°–160° and preferably about 90°–100°. As described briefly earlier, the surfaces of the cleft 70 merge into generally cylindrical portions 68 which then merge into rounder corner portions 69 at each end of the valve element, which may form fluid seals with the inner walls of the valve housing. The rounded corners terminate in the relatively flat end surfaces 64 and 66 of the valve body. The bore 20 through the valve body preferably tapers slightly inwardly from each end to the midpoint of the valve body, as best seen in FIGS. 2 and 8.

Although the preferred configuration of the valve element 14 has a valve body that is approximately hour glass shaped, alternative valve element configurations may be used. For example, a uniformly cylindrical configuration which lacks a recessed mid-section, may be satisfactory. Other alternative embodiments of the valve element, such as spheres and oblongs, may also be used without departing from the scope of the present invention.

Figure 6:
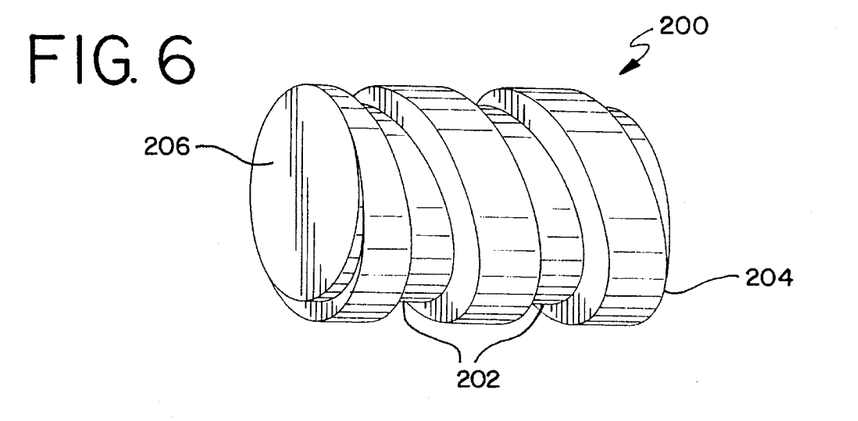
FIG. 6 is a perspective view of an alternative embodiment of a valve element embodying the present invention.

Another alternative valve element design is shown in FIG. 6. The valve element 200 shown there has a spirally grooved flow pathway 202 along its external surface of the valve body and extending fully between first end 204 and second end 206, allowing fluid to flow around and past valve element 200. Longitudinal grooves on the surface of the valve element body also could be used. These grooved valve elements, of course, should fit snugly within the valve element chamber, such as the bore 18 of the second rigid member 12, so that the surface of the valve element between the grooves seal against the inside surface of the valve element chamber to constrain the fluid to move within the grooves.

With valve elements having the flow path defined at least in part by grooves on the external surface of the valve body, compression of the grooved valve element causes size reduction or closure of the grooves while maintaining the seal between the peripheral surface of the valve element and the surface of the bore of the second rigid member.

In another valve element design, the valve element body may be generally cylindrical or oval, lack a through bore or external grooves, but permit fluid flow to and from the bores of the rigid members by allowing flow over its outer surface. The outer diameter of this valve element body should be slightly less than the internal diameter of the bore of the second rigid member which forms the valve element chamber to provide a gap through which fluid may pass. One or more raised surfaces (such as raised bumps or ridges) may be provided at each end of the valve element body to hold the valve element spaced from the internal surface of the bore of the second rigid member. During compression, the diameter of the valve element would expand to contact the surface of the bore of the second rigid member thereby closing the gap between the external surface of the valve element and the bore surface and restricting the flow of fluid around the valve element.

For each of the valve elements in which fluid flows from end to end over the exterior surface of the valve element, whether in grooves or simply over the surface of the valve element, the ends of the valve element chamber, such as surface 32 of the cylindrical body portion 26 and the shoulder 62 of the second rigid member 12 do not sealingly contact the valve element. Instead, the second end of the first rigid member and the shoulder of the second rigid member are preferably slotted to define one or more radial channels to allow the flow of fluid from the bores of the first and second rigid members to and from the peripheral surface of the valve element. In the embodiments where fluid flows over the exterior surface of the valve element, it also will be appreciated by those of ordinary skill in the art that leakage between the rigid members in this embodiment may be prevented by various means, including insertion of one or more 0-rings between the exterior surface of the cylindrical body portion and the interior of the tubular body portion.

Further, although the preferred embodiment contains a single bore passing through valve element 14, it is also within the scope of the present invention that the valve element may have more than one bore, for example 2 to 5 bores, passing through it. In operation, multiple bores may allow some bores to close while others remained open, thus regulating the fluid flow through the flow control valve.

Figure 5:
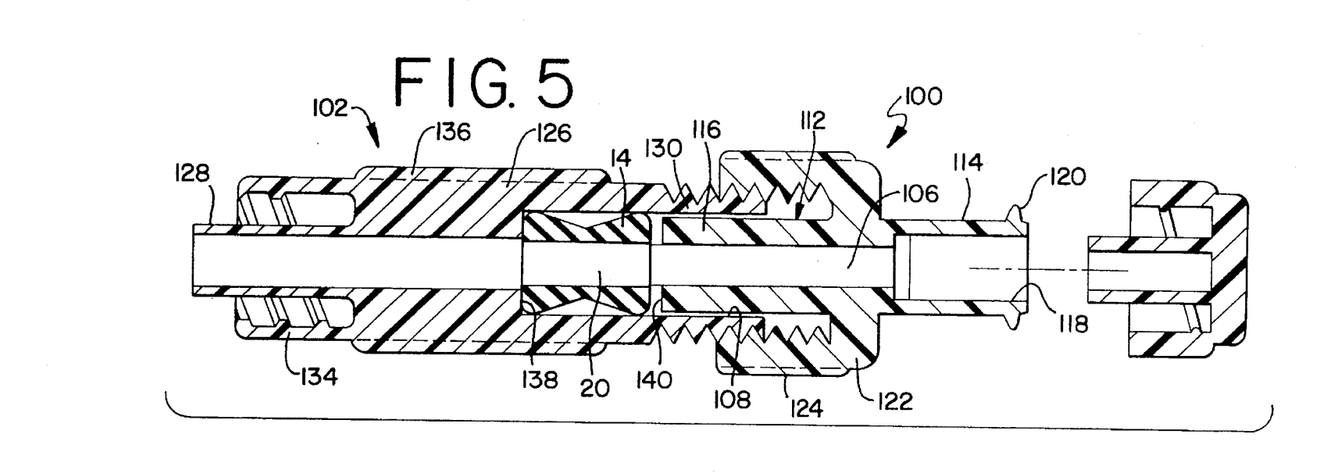
FIG. 5 is a cross-sectional view of an alternative embodiment of the flow control valve and valve element of the present invention with the flow path therethrough open.

In a further alternative embodiment of the present invention, as best seen in FIG. 5, the first and second rigid members, 100 and 102 respectively, are threadedly instead of slidably attached. In that embodiment, the compression of the valve element 14 and therefore the flow rate may be infinitely controlled by relative rotation of the rigid members 100 and 102.

As in the preferred embodiment, the first rigid member 100, second rigid member 102 and valve element 14 each define a bore, 106, 108 and 20 respectively, which together define the flow path passing coaxially through the flow control valve. The first rigid member 100 has a cylindrical body portion 112 with a first end 114 and a second end 116. The first end 114 of first rigid member 100 is adapted for attachment to any desired conduit and, as depicted in FIG. 5, may embody a female luer 118 with a thread 120 to facilitate luer lock attachment to a corresponding male luer. Other forms of attachment may be substituted at the first end 114 of the first rigid member 100 without departing from the scope of the present invention.

The second end 116 of cylindrical body portion 112 has an external diameter slightly smaller than the internal diameter of bore 108 of the second rigid member, such that the second end 116 of the cylindrical body portion 112 may be received slidably within bore 108 when the valve is assembled as in FIG. 5. To hold the rigid members together, the first rigid member 100 has an internally threaded collar 122 that partially overlaps the second end 116 of the cylindrical body portion 112.

The second rigid member 102 of the flow control valve has a generally tubular body portion 126 with a first end 128 and a second end 130. The first end 128 of the second rigid member 102 is adapted for conduit attachment and, as depicted in FIG. 5, may take the form of a male luer with a threaded ring 134 facilitating locking luer attachment with a corresponding female luer. As was the case with the preferred embodiment, various alternative forms of attachment may be substituted at the first end 128 of the second rigid member without departing from the scope of the present invention.

The second end 130 of the tubular body portion 126 of the second rigid member 102 is threaded for a distance along its outer surface to engage the threaded collar 122 of the first rigid member 100.

The preferred valve element 14 in the alternative embodiment is identical to the hour-glass shaped valve element described above, although the alternative valve elements also could be used.

When the flow control valve is assembled, as best seen in FIG. 5, the second end 116 of cylindrical body portion 112 is received within bore 108 of the second rigid member 102. Valve element 104 is located within valve element chamber defined between bore 108, shoulder 138 of the tubular body portion 126 and the end surface 140 of the second end 116 of the cylindrical body portion 112.

The threaded collar 122 of the first rigid member 100 overlaps the threaded exterior of the second end 130 of the second rigid member 102, such that rotating the rigid members 100 and 102 relative to each other axially moves the second end 116 of the cylindrical body portion 112 axially within bore 108 of the tubular body portion 126.

The first and second rigid members, 100 and 102 respectively, are rotationally threadedly movable between at least first and second positions. In the first position, the distance between shoulder 138 and end surface 140 (and the corresponding valve element chamber size) is sufficiently small that valve element 104 is fully compressed and bore 110 is fully closed. In the second selected position, as best seen in FIG. 5, the distance between shoulder 138 and end portion 140 (and the corresponding valve element chamber size) is sufficiently large that the valve element is relaxed and the bore 110 is fully open. Due to the threaded operation of the flow control valve, the first rigid member 100 and second rigid member 102 may be infinitely varied between the first and second selected positions and, as such, the size of the valve element chamber and the degree of compression of the valve element and corresponding degree of bore size may also be infinitely varied.

To facilitate rotation of the rigid members 100 and 102, raised ridges 124 and 136 may be provided on external surface of threaded collar 122 of first rigid member 100 and tubular body portion 126 of second rigid member 102 to create textured frictional body surfaces.

In a still further embodiment, an access passage (not shown) may be located in the second rigid member 102 between shoulder 138 and second end 130 of the tubular body portion. This access passage into the valve element chamber facilitates puncturing the valve element with a hypodermic needle, thus allowing the valve element to be used as a septum for emergency delivery of drugs or other fluid directly into the flow path through the flow control valve.

Figure 7:
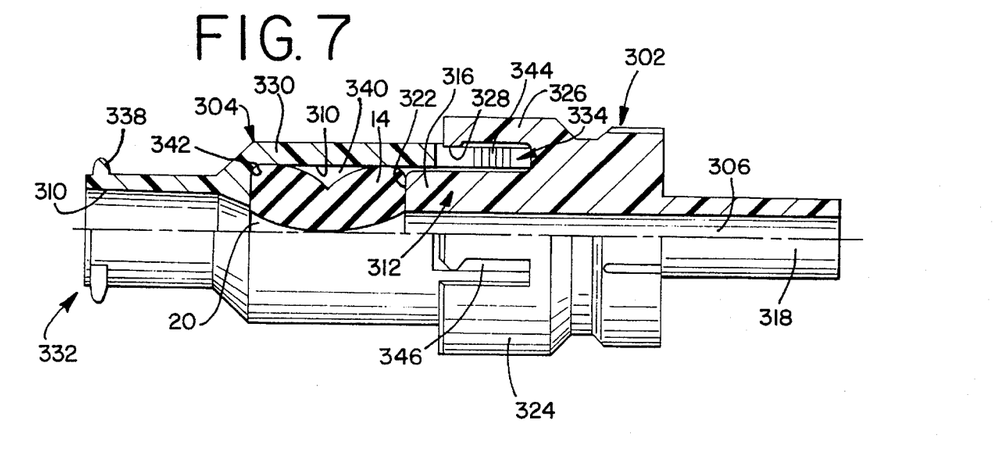
FIG. 7 is a side view, partially in cross-section, of an alternative embodiment of the flow control valve of the present invention.

FIG. 7 depicts another embodiment of the present invention having a modified rigid housing with the valve element 14 located therein. In this embodiment, the housing is comprised of a first rigid member 302 and second rigid member 304. Bores 306, 20 and 310 extend through the first rigid member 302, valve element 14 and second rigid member 304, respectively and define a fluid flow path through the valve. As explained below, rigid members 302 and 304 may be moved axially relative to each other to regulate size of the valve element chamber and the compression of the valve element 14 and, thus, the fluid flow through the flow control valve.

The first rigid member 302 comprises a generally hollow cylindrical body portion 312 through which bore 306 extends. From the body portion 312, the bore 306 extends through a tapered male luer fitting 318. The rigid body member 302 may also include a threaded collar if desire for providing a luer lock with a corresponding female luer connector.

The end portion 316 of the cylindrical body portion is sized for receipt within the second rigid member 304, with the very end surface 322 of the cylindrical body portion abutting one end of valve member 14 when the flow control valve is assembled. As indicated earlier, the side walls of the valve element may form a fluid seal with the inside surface of the bore 310. Also, the end surfaces of the valve element may sealingly contact end surface 322 and shoulder 342. In the event the end of the valve element is not in sealed contact with the end surface 322, one or more o-rings, such as a pair of spaced-apart o-rings, may be provided on the end portion 316 to provide a liquid-tight seal between end portion 316 and the surface of bore 310. Such o-rings may also be used in the other disclosed embodiments, as desired.

To aid in controlling the compression of valve element 14, the cylindrical body portion 312 includes an outer sleeve 324 that extends annularly around and is spaced from the cylindrical body portion 316. The sleeve 324 includes one or more retaining arms 326 with inwardly directed protrusions or hooks 328 that cooperate with the second rigid member 304 to control the relative axial positioning of the first and second rigid members, 302 and 304, and the compression of valve element 14.

The second rigid member 304 of the valve housing has a generally hollow tubular body portion 330 with first and second ends, 332 and 334 respectively. The first end of the second rigid member 332 is in the form of a female luer lock fitting with a tapered inner bore 310 and an end thread or flange 338 facilitating a luer lock with a corresponding male luer (not shown). The second end 334 of the tubular body portion, in part defines a large central cavity 340 having an interior shoulder 342 against which the valve element 14 rests.

The exterior surface of the tubular body portion 330, adjacent second end 334, carries one or more rows of raised ribs or saw teeth 344 which are adapted to contact the inwardly directed protrusions 328 of the retaining arms 326. The raised ribs or saw teeth 344 extend only partially around the surface of the second member leaving smooth surface areas 346 therebetween on the outer surface of the second rigid member, which allow the release of rigid members 302 and 304 when the retaining arms 326 are related to positions overlying the smooth release surfaces 346.

In the flow control valve shown in FIG. 7, the end portion 316 of the cylindrical body portion 312 extends into the tubular body portion 330, and defines one end of the valve cavity 340. The valve element 14 is located within the tubular body portion between the end surface 322 of the cylindrical body portion 312 and the shoulder 342 of the tubular body portion 330. The volume of cavity 340, and thus the degree of compression of the valve element 14, is determined by the distance between shoulder 342 and end surface 322. The cylindrical body portion 312 is movable axially between a first position relative to shoulder 342, wherein valve element 14 is compressed enough to block fluid flow therethrough, and a second position spaced farther from shoulder 342, wherein the valve cavity is larger and valve element 14 is sufficiently relaxed to fully open the flow path and allow fluid flow therethrough. The rigid members 302 and 304, also may be positioned at intermediate positions between the first and second positions, thus allowing intermediate degrees of compression and corresponding fluid flow.

To maintain a desired state of valve element compression, the first rigid member 302 may be rotated such that retaining arms 326 overlap the ribs or saw teeth 344 of the tubular body portion 330. The axial location of ribs 344 on tubular portion 330 correspond to the various distances between end surface 322 and shoulder 342 and thus various degrees of valve element compression. As the end surface 322 of cylindrical body portion 322 is forced closer toward shoulder 342 of tubular body portion 330, the protrusions 328 of the retaining arms 326 are forced over the ribs 344 of tubular body portion in a ratchet-like fashion. Movement of end surface 322 away from shoulder 342 of the tubular body portion is prohibited due to the protrusion-rib interference.

To release the ratchet-like engagement between the protrusion 328 and ribs or saw teeth 344, the rigid members are rotated such that protrusions 328 are moved into position over the release surfaces 346 of tubular body portion 330, allowing the rigid members to axially separate sufficiently for further relaxation of the valve element, with increase in the flow therethrough.

Figure 9:
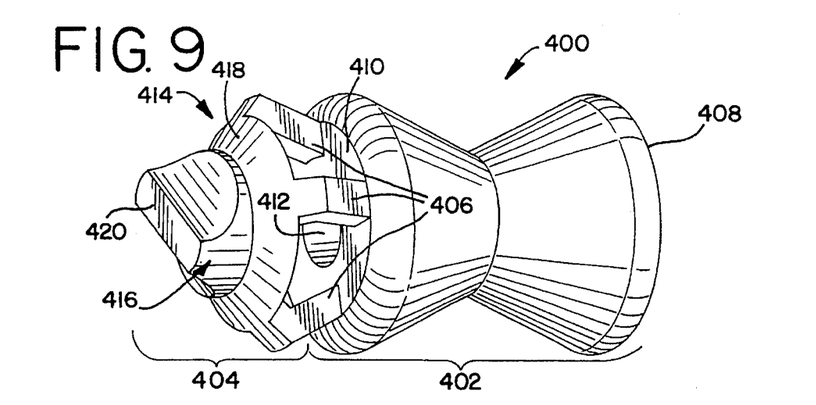
FIG. 9 is a perspective view of an alternative two-stage embodiment of the valve element of the present invention.

A still further embodiment of the valve element of the present invention is depicted in FIG. 9. FIG. 9 shows a two-stage valve element 400 that comprises a first valve body 402, a second valve body 404 and a plurality of resilient legs 406 connecting valve bodies 402 and 404.

The first valve body 402 is essentially as previously shown and described in FIGS. 1, 2, 3, 7 and 8, and has first and second ends, 408 and 410, respectively, with a bore 412 extending therethrough. The second end 410 of first valve body 402 carries a plurality of resilient legs 406 that connect the first valve body 402 and second valve body 414, and allow the valve bodies to be moved axially relative to each other. Each leg is formed by a pair of leg segments that extend at an outward angle and are joined at an outwardly directed vertex so as to bend or collapse outwardly when the second valve body is moved toward the end 410 of the first valve body, as seen for example in FIG. 12. Although shown with four such legs, as few as two legs and as many as eight or more may be used.

Second valve body 404 has a generally conical lower section 414 and a cylindrical upper section 416. The lower section has an angled or conical sealing surface 418 which is adapted to seat against a mating surface of the rigid housing containing the valve element to regulate the flow of fluid therethrough, as will be described below. The upper segment of legs 406 form a continuation of the surface of conical sealing surface 418.

Figures 10, 12:
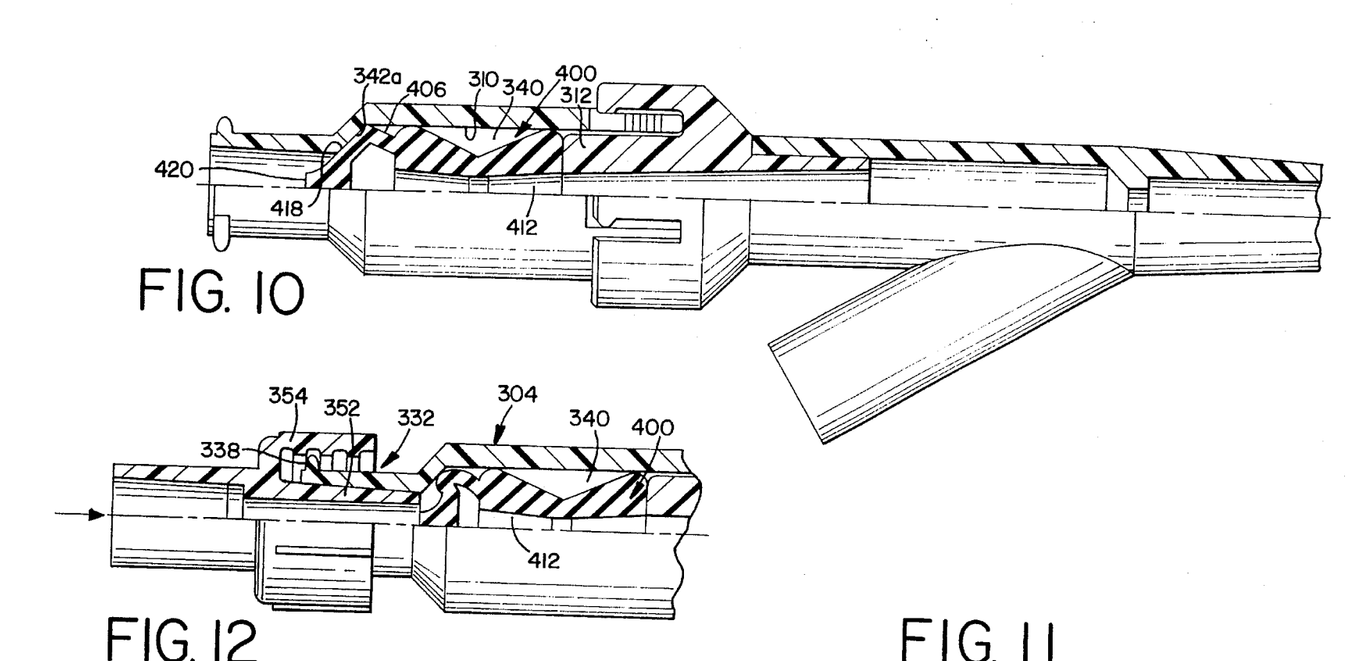
FIG. 10 is side view, partially in cross-section, of an alternative embodiment of the flow control valve of the present invention incorporated into an access device to a fluid delivering circuit and, employing the two-stage valve element shown in FIG. 9.
FIG. 12 is a partial view of the valve of FIG. 10, depicting introduction of a male luer fitting into the inlet end of the flow control valve to engage and open the two-stage valve element.

The cylindrical upper section 416 of the second valve body 404 tapers to a narrow raised contact surface 420 which allows the second valve body to be depressed by the end of a tubular flow conduit, such as the open end of a male luer as shown in FIG. 12, without blocking the end of the conduit. In other words, the narrow contact surface allows a substantial part of the end of the fluid conduit to remain open, for receiving or injecting fluid through the valve, while simultaneously depressing the second valve body.

The two-stage valve element 400 is adapted for use in a flow control valve having a modified rigid housing. As seen in FIG. 10, the rigid housing is essentially similar to that shown in FIG. 7, except that the tubular body portion is slightly longer and the shoulder 342a of tubular body portion is disposed at approximately a 45 degree angle, corresponding to the angle of the sealing surface 418 of second valve body 404. Accordingly, shoulder 342a forms a valve seat surface around bore 310 so that when valve element 400 is disposed within cavity 340, the sealing surface 418 of the second valve body 404 contacts the shoulder 342a sufficiently tightly to block the bore and prevent flow therethrough.

In the flow control valve containing two-stage valve element 400, fluid flow through the valve may be regulated independently by either the first valve body 402 or second valve body 404. The flow direction will normally be from left to right in FIG. 10, i.e., past the second valve body 404 and then through the first valve body 402.

Figure 11:
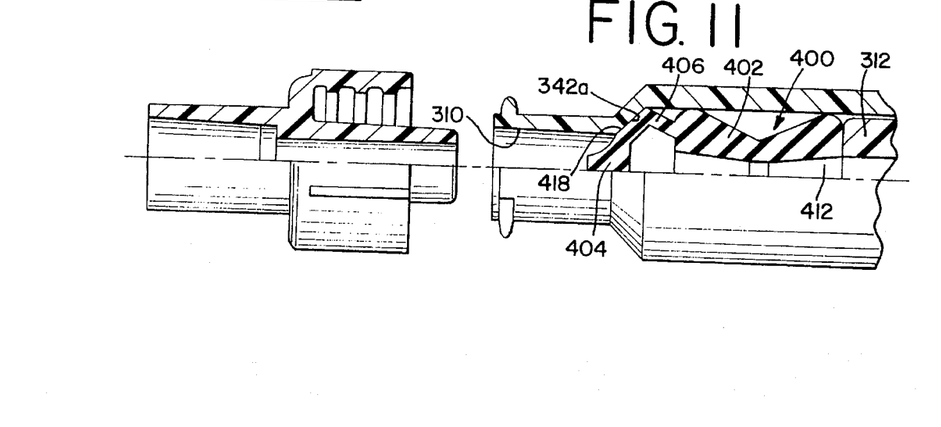
FIG. 11 is partial view of the valve of FIG. 10, showing impending introduction of a male luer fitting into the inlet end of the flow control valve of FIG. 10.

As best seen in FIGS. 10 and 11, when the cylindrical body portion 312 of the first rigid member 302 is in the "second" position relative to shoulder 342a, and bore 412 through the first valve body 402 is open, there is still enough axial pressure exerted on the valve element to hold the sealing surface 418 against shoulder 342a to block flow through bore 310. Sealing contact between surface 418 and shoulder 342a is maintained due to the axial force exerted by resilient legs 406, which transmit to the second valve body 404 the axial force exerted on the first valve body 402 by the cylindrical body portion 312. In this normally closed position of the second valve body, the second valve body remains spaced from the first valve body by the legs 406.

Fluid flow from bore 310 to bore 412 is permitted when sealing surface 418 is moved away from shoulder 342a. As best viewed in FIG. 12, this movement may be accomplished by inserting an elongated flow conduit, such as male luer 352, into the female luer of the first end 332 of the second rigid member 304. Male luer 352 is sufficiently long to engage against contact surface 420, depressing the second valve body to disengage the sealing surface 418 from shoulder 342a and thereby opening the valve.

Because the tip male luer 352 of the flow conduit contacts only the narrow contact surface 420, the remaining portion of the luer tip remains open to allow fluid to flow from the male luer 352, between the sealing surface 418 and shoulder 342a and between the legs 406 into bore 412 as generally depicted by the arrows in FIG. 12. For example, the male luer may be attached to a syringe or other fluid source for introducing liquid into the valve housing. Alternatively, fluid may flow in the reverse direction from the valve housing into the male luer, if desired, when the second body is in the open position.

Male luer 352 may be held within female luer 332 by the luer lock engagement of flange 338 and inwardly threaded collar 354. As will be appreciated, because resilient legs 406 bias the second valve body to a closed position seated against shoulder 342a, withdrawal of male luer 352 from the female luer 332 results in the automatic closure of valve element. Upon removal of the male luer, resilient angled legs 406 tend to revert to their prior, unbent configuration, thus forcing the sealing surface 418 into sealing contact with shoulder 342a.

As depicted in FIG. 10, the dual stage valve element also allows introduction of fluid into a fluid path. As shown there, the valve housing is attached to one branch of a Y-fitting 422. The other branches may form part of a continuous liquid flow path. By depressing the second valve body, direct access is provided for injecting liquid directly into the flow path from the blunt end of a fluid conduit, for example, directly through the male luer of a syringe or other fluid source. In medical applications, for example, this would allow for injection of liquids into a fluid stream without the need to use a needle for piercing a resealable septum or diaphragm. Insertion of a conduit, such as the male luer depicted in FIG. 10, automatically allows access through the flow path, while withdrawal of the conduit causes automatic closure of the flow path, so long as the first valve, if present, remains in the open position.

It will be appreciated by those of ordinary skill in the art that the application of such a "two-stage" valve design is not limited to valve elements having hourglass shaped first valve bodies. The second valve body and resilient legs shown in FIGS. 9–12 may be combined with any of the wide variety valve elements discussed above, e.g., the valve element of FIG. 6, to achieve the same results.

Figure 13:
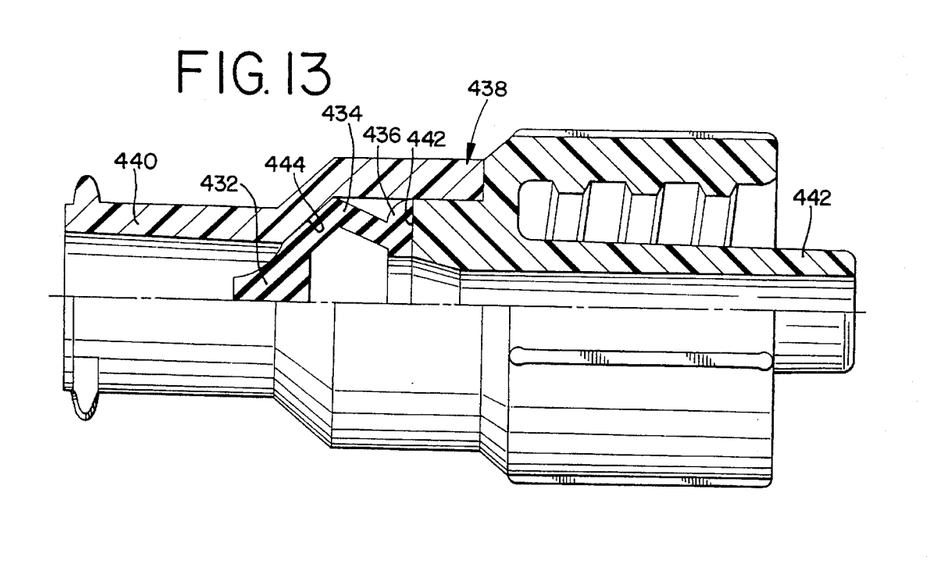
FIG. 13 is a side view, partially in section, of a valve using an alternative single-stage valve element of the present invention.
Figure 14:
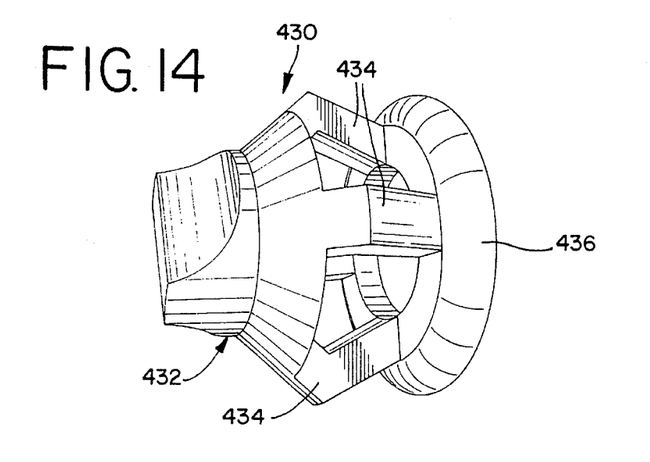
FIG. 14 is a perspective view of the single-stage valve element employed in FIG. 13.

In addition, the second valve body may be used independently, and without the first valve body, as a single stage valve, as shown for example in FIGS. 13 and 14. FIG. 14 depicts the alternative valve element, generally at 430. This alternative valve element has a valve body portion 432 that is essentially the same to the second valve body 404 described earlier in connection with FIGS. 9–12, and a plurality of spaced-apart resilient legs 434 that are also essentially the same as the resilient legs 406 described in connection with those Figures. This valve element is similarly made of resilient or elastomeric material such as natural rubber, silicone, or other synthetic material.

The alternative valve element 430 differs from the previous embodiment primarily in that there is no first valve body that is operable to control flow. Instead, the resilient legs are attached to a mounting base or supporting ring 436.

FIG. 13 depicts the valve element 430 mounted in a two-part rigid housing 438. One end of the housing terminates in a female luer fitting 440 and the other end terminates in a male luer fitting 442, although other means of attachment may also be used. The valve element 430 is captured between the two parts of housing in a normally closed position, with the mounting base 436 resting against interior shoulder 442 and the valve body 432 engaged in liquid-tight contact against tapered shoulder 444 to normally block the flow of liquid through the female luer. As with the embodiment described earlier, insertion of a fluid conduit, such as male luer, into the female luer fitting depresses the valve body to allow the introduction of fluid into the valve housing through the female luer fitting. When the fluid conduit or male luer is withdrawn, the resilient legs automatically return the valve body to a normally closed position in liquid-tight engagement with the shoulder 442.

While the invention has been described in connection with the preferred and various alternative embodiments thereof, it will be appreciated by those skilled in the art that various changes and modifications can be made without departing from its spirit. It is therefore intended that the coverage afforded applicant be limited only by the claims and their equivalents.

We claim:

1. A flow control valve comprising:
   first and second rigid members axially movable along a generally common axis between a plurality of axial positions, said first and second rigid members being relatively rotatable about said axis between a first rotational position that allows axial movement of said first and second rigid members and a second rotational position that prevents axial separation of said first and second rigid members;
   a chamber defined between said rigid members, the volume of said chamber being selectively variable depending on the relative position of said rigid members;
   a resilient valve element including at least a first valve body disposed within said chamber; and
   a fluid flow path defined through said rigid members and said chamber to provide a flow path through said flow control valve, whereby the size of said flow path through said chamber may be varied by varying the degree of compression of said valve body by said rigid members.

2. The flow control valve of claim 1, wherein said flow path extends along said axis through said valve body and wherein the size of said flow path through said valve body may be uniformly varied by compression of said valve body so as not to disturb the laminar flow of the fluid passing therethrough.

3. The flow control valve of claim 1, wherein said valve element comprises a fluid inlet, a fluid outlet, and a flow path therebetween defined in said first valve body, whereby the size of said flow path through said first valve body may be varied by compression of said first valve body, and,
   a second valve body resiliently carried by said first valve body and movable relative to said first valve body between first and second positions, said second valve body blocking fluid flow through said flow path in said rigid members when in said first position and allowing flow when in said second position.

4. A flow control valve in accordance with claim 1, wherein said first valve body is generally hourglass-shaped and has a first end defining said fluid inlet, a second end defining said fluid outlet, said flow path extending between said inlet and outlet.

5. The flow control valve of claim 4 wherein said flow path has a generally hour-glass shape in said first valve body so that said flow path tapers inward from said inlet and outlet to a midpoint in said first valve body.

6. The flow control valve of claim 4 wherein said first valve body comprises a generally cylindrical surface portion that merges into a rounded corner at said inlet and said outlet of said first valve body.

7. A flow control valve in accordance with claim 1 wherein one of said rigid members defines a valve seat surface around said flow path, and said valve element further comprises a second valve body resiliently carried by said first valve body and movable relative to said first valve body between first and second positions,
   said second valve body sealingly contacting said valve seat surface and closing said flow path when said second valve body is in said first position and allowing flow when in said second position.

8. The flow control valve of claim 7 wherein said second valve body and said first valve body are connected by a plurality of spaced apart resilient legs that extend between said first valve body and said second valve body.

9. The flow control valve of claim 1 wherein said first rigid member includes a generally tubular member open at one end and having a shoulder therewithin spaced from said one end; the other rigid member including an extension slidably received through said open end of said tubular member; and said valve element being disposed within said tubular member and adapted to be compressively engaged between said shoulder and said extension.

10. The flow control valve of claim 1 wherein one of said rigid members has at least one retaining arm for releasably engaging the other rigid member.

11. The flow control valve of claim 10 wherein said retaining arm includes a hook and the other of said rigid members includes a hook engaging surface, said hook being engaged with said hook engaging surface when said rigid members are in a first axial position.

12. The flow control valve of claim 11 wherein said retaining arm is attached at one end to said one of said rigid members and extends freely to a second end, said hook being located at a position spaced from the attached end of the retaining arm, and said rigid housing further includes a fulcrum element disposed at a location between said hook and said fixed end of said retaining arm such that application of pressure on said retaining arm between said fulcrum element and said fixed end disengages said hook from said hooking surface.

13. The valve element of claim 1, wherein said first and second rigid members are relatively movable between more than two axial positions corresponding to different degrees of compression of said valve element to vary the size of said flow path through said chamber.

14. The flow control valve of claim 1 wherein said first rigid member includes a retaining arm and said second rigid member includes a smooth axial portion and an adjacent portion comprising a plurality of retaining arm-engaging elements disposed serially on said adjacent portion and wherein in said first rotational position said retaining arm is aligned with said smooth axial portion to allow axial motion of at least one rigid member and wherein in said second rotational position said retaining arm is aligned with at least one of said retaining arm-engaging elements to prevent axial separation of said rigid members.

15. The flow control valve of claim 1 wherein said first valve body has a first end, a second end and an exterior surface and includes a channel defined in the exterior surface of said first valve body that extends between said first and second ends, said channel being adapted to define said fluid flow path.

16. The flow control valve of claim 15 wherein said channel is generally in a spiral around said exterior surface.

17. The flow control valve of claim 1 further comprising a male luer fitting on an end of said first rigid member opposite of said chamber.

18. The flow control valve of claim 1 further comprising a female luer fitting on an end of said second rigid member opposite of said chamber.

* * * * *